United States Patent [19]

Wilp

[11] Patent Number: 4,671,269
[45] Date of Patent: Jun. 9, 1987

[54] PERSONAL ION INHALER DEVICE
[76] Inventor: William A. Wilp, 103 Falmouth Dr., Ballwin, Mo. 63011
[21] Appl. No.: 861,448
[22] Filed: May 9, 1986
[51] Int. Cl.⁴ .................. A61M 15/00; A61N 1/44
[52] U.S. Cl. ..................... 128/202.25; 128/204.23
[58] Field of Search ............... 128/202.25, 202.21, 128/203.23, 204.13, 204.23

[56] References Cited

U.S. PATENT DOCUMENTS 3,096,762 7/1963 Winchell .............. 128/202.25
3,320,953 5/1967 Rindner .............. 128/202.21

FOREIGN PATENT DOCUMENTS 653626 5/1963 Italy ................... 128/202.25
717242 10/1966 Italy ................... 128/202.25
1045883 10/1966 United Kingdom ........... 128/202.25
1138173 2/1985 U.S.S.R. ................ 128/202.25

Primary Examiner—Henry J. Recla
Attorney, Agent, or Firm—Rogers, Howell, Moore & Haferkamp

[57] ABSTRACT

A personal ion inhaler comprising a tube with an air passage therethrough having an inlet and outlet end. A filter means is secured in the air passage near the inlet end. A mouthpiece is secured at the outlet end. There is an ionization chamber in the air passage having a conductive lining and an electrode. A shuttle switch only connects a charge storage capacitor to the electrode when air is drawn through the inhaler to ionize the air passing the electrode.

20 Claims, 4 Drawing Figures

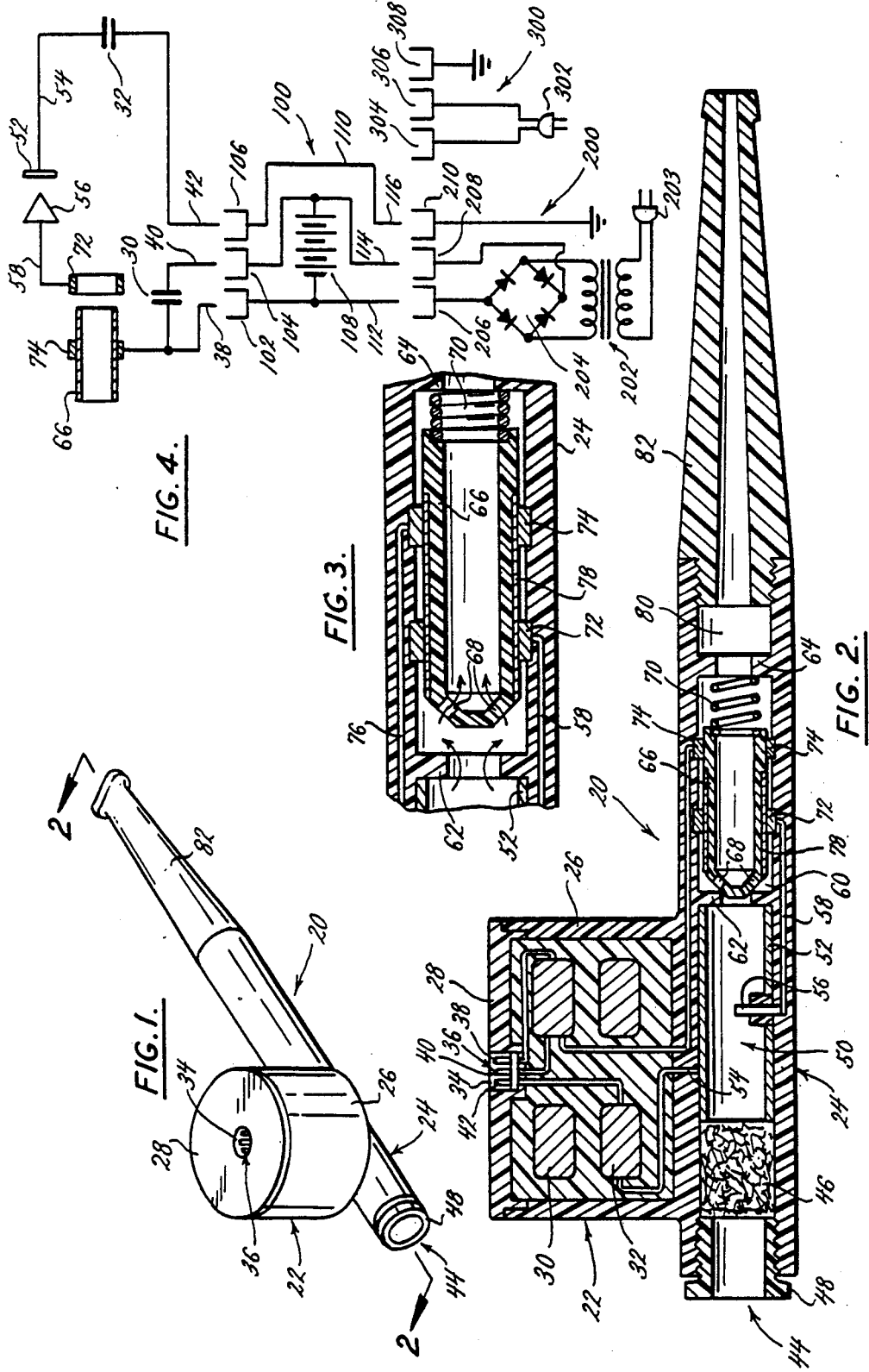

PERSONAL ION INHALER DEVICE

BACKGROUND AND SUMMARY OF THE INVENTION

This invention relates to a device for producing negative ions, and in particular to a portable device for producing negative ions for inhalation.

The inhalation of negative ions is recognized as being generally therapeutic. Benefits to the pulmonary system and central nervous system have been credited to the inhalation of negative ions. Negatively ionized air has been used in treating patients suffering from high blood pressure, ulcers, and burns. Increased resistance to fatigue and a general feeling of well-being have also been attributed to the inhalation of negative ions.

There have been negative ion generators in the past, but these have been large, cumbersome devices. Many of these devices discharge ions to the room, although there were some devices equipped with mouthpieces. None of these devices were portable, personal devices with a self-contained power supply that were convenient to carry around and use as desired.

Some of these prior devices produced negative ions by charging and vaporizing a liquid. For example, Schwedenberg et al., U.S. Pat. No. 1,984,159, and Wehner, U.S. Pat. No. 3,194,236. Other prior devices utilized an electrolysis reaction. For example, Irving, U.S. Pat. No. 596,936. Another, Winchell, U.S. Pat. No. 3,096,762 ionized air as it was drawn through a mask. As noted above, none of these devices was truly portable or personal, they used large amounts of power and required external power sources. Thus, they were all inconvenient to use and their use was limited.

The production of negative ions is adversely affected by large air-borne particles which diminish the efficiency of the charging device and produce ions of extremely short life. Negative ions have short lives, anyway, ranging from milliseconds to about thirty seconds, and thus large quantities must be produced to provide an effective amount for inhalation.

The present invention is a portable, personal negative ion generator. The device is extremely compact and has an internal power supply so that it is truly portable and can be carried and used anywhere. The power supply is preferably rechargeable and/or connectable to any convenient power supply to preserve the storage device. The preferred embodiment of the device generally resembles a smoking pipe. This makes the device more acceptable for public use. Furthermore, used this way the device generates ions immediately before ingestion to maximize the use of the short-lived ions. The device also preferably includes a filter to remove large airborne particles that diminish the efficiency of the ion generator.

The device preferably includes a shuttle switch actuator that only powers the ion generator when the user draws air through the device. This conserves energy, allowing for a smaller energy storage unit and a more compact device over all. Furthermore, it maximizes the use time for a given energy supply.

Generally, the device comprises a hollow tube with a mouthpiece at one end and a filter at the other. An energy storage device can be mounted on the tube much like the bowl on a pipe. An ion generator is disposed in the tube. A shuttle switch is also disposed in the tube and connects the ion generator to the energy storage device only when air is drawn through the tube.

The device of the present invention is of simple construction. It is compact and portable and can be used anywhere. The device filters out large particles and provides ions at the point of consumption for maximum efficiency. A special actuator conserves energy allowing for a more compact device and longer operating time. The device makes the therapeutic benefits of negative ion inhalation more available. Furthermore, the device is a safe and convenient substitute for tobacco smokers and may help such smokers reduce or quit their smoking.

BRIEF DESCRIPTION OF THE DRAWINGS

FIG. 1 is an orthogonal view of a personal ion inhalation device constructed according to the principles of this invention;

FIG. 2 is longitudinal cross-section of the inhalation device taken along the plane of line 2—2 in FIG. 1;

FIG. 3 is an enlarged view of the shuttle switch for selectively connecting the ion generator and the energy storage device;

FIG. 4 is a schematic diagram of the device.

DETAILED DESCRIPTION OF THE PREFERRED EMBODIMENT

A personal ion inhaler device constructed according to the principles of this invention is indicated generally as 20 in FIGS. 1 and 2. Inhaler 20 comprises a generally cylindrical body section 22 mounted on a hollow tubular section 24, like a bowl on a pipe.

Body section 22 comprises a housing 26, made from a non-conductive material, and a cap 28. A charge storage device 30 is positioned in housing 26. This charge storage device 30 can be a battery or a capacitor, but is preferably a capacitor. An optional charge drain device 32 can also be positioned in housing 26. This charge drain 32 device is preferably a capacitor.

The center of cap 28 has a socket opening 34 in which a three-pin connector 36 is disposed. Two pins 38 and 40 are connected to the opposite leads of the charge storage capacitor 30 to permit the capacitor 30 to be recharged. The third pin 42 is connected to the charge drain capacitor 32.

The tubular section 24 has an inlet end 44 in which a filter 46 is positioned, and held in place with a retaining member 48 threadedly engaged in inlet end 44. Retaining member 48 can be removed to replace filter 46. Behind filter 46 is an ionization chamber 50. Chamber 50 has a conductive lining 52 which is connected by lead 54 to charge drain capacitor 32. The ion generator is a corona discharge type, comprising an electrode 56. Electrode 56 is preferably made of carbon fiber to suppress the production of toxic gases during ionization, especially ozone. A lead 58 extends from electrode 56.

Immediately behind ionization chamber 50 is a switch chamber 60 defined at the forward end by an annular partition 62 and at the rearward end by an annular partition 64. A bullet-shaped shuttle 66 is mounted in switch chamber 60. The cross-section of shuttle 66 is slightly less than that of the switch chamber 60 so that the shuttle 66 can freely slide therein. Shuttle 66 is generally hollow. The front end of shuttle 66 is substantially closed, but has small ports 68 for the passage of air. The rear end of shuttle 66 is substantially open. Shuttle 66 is resiliently biased forwardly in switch chamber 60 by a coil spring 70 extending between the rear end of shuttle 66 and partition 64.

A first contact ring 72 is mounted in switch chamber 60 and is connected by lead 58 to electrode 56 in ionization chamber 50. A second contact ring 74 is mounted in switch chamber 60, axially spaced behind first contact ring 72, and is connected by a lead 76 to the charge storage capacitor 30. The forward portion of shuttle 66 has a conductive coating 78. Coating 78 does not extend to the back of shuttle 66, and thus when shuttle 66 is in its normal forward-biased position, there is no connection between the contact rings 72 and 74, but when shuttle 66 is drawn back, as described below, there is a connection between the contact rings 72 and 74, completing the circuit between the charge storage capacitor 30 and the ionizer electrode 56. Immediately behind switch chamber 66 is a chamber 80 into which substances such as medicines, scents, flavorings can be put to introduce such substances into the air stream.

A mouthpiece 82 is threadedly engaged to the outlet end of tube section 24. Drawing air through mouthpiece 82 draws shuttle 66 rearwardly into contact with both contact rings 72 and 74. This completes the circuit between contact rings 72 and 74, energizing electrode 56 to ionize the air passing by electrode 56.

Ion generator 20 can be recharged, for example, by connection with portable charge unit 100. Portable charge unit 100 has three clips 102, 104, and 106, for engaging pins 38, 40, and 42, respectively, of ion inhaler 20. Charge unit 100 has a charge storage device 108, the terminals of which are connected to clips 102 and 104 so that when portable charge unit 100 is connected to ion inhaler 20, storage device 108 is connected to the charge storage capacitor 30 so that storage device 108 can charge the charge storage capacitor 30. Portable charge unit 100 also has a bypass 110 connected to clip 106 so that when portable charge unit 100 is connected to ion inhaler 20, bypass 110 is connected to the charge drain capacitor 32 to discharge any accumulated charge. Charge unit 100 also has three pins 112, 114, and 116. These pins are connected to clips 102, 104, and 106, respectively.

A rectified A.C. charge unit 200 can be used to recharge portable charge unit 100 or ion inhaler 20. Charge unit 200 comprises a transformer 202 which can be connected to an A.C. power source, such as a standard household current line through plug 203. Charge unit 200 includes a full wave bridge rectifier 204 which rectifies the A.C. into D.C. to charge storage device 108, as known in the art. Charge unit 200 has three clips 206, 208, and 210 for engaging pins 112, 114, and 116, respectively, of portable charge unit 100 or for engaging pins 38, 40, and 42, respectively, of ion inhaler 20. Clip 206 is connected to the negative terminal of rectifier 204. Clip 208 is connected to the positive terminal of rectifier 204. Thus, clips 206 and 208 provide a D.C. charge current to storage device 108 when connected to charge unit 100 or to charge storage capacitor 30 when connected to ion inhaler 20. Although not shown, one or more current limit resistors, or other protective or filtering circuitry may be provided, as known in the art. Clip 210 is connected to ground, to ground the charge drain capacitor 32 when connected thereto. Ion inhaler 20 can be connected directly to charge unit 200 or portable charge unit 100 can be interposed between ion inhaler 20 and charge unit 200.

A D.C. charge unit 300 can be used to recharge portable charge unit 100 or ion inhaler 20. D.C. charge unit 300 can be connected to a D.C. power source, such as an automobile electrical system with plug 302. The D.C. charge unit 300 can include some means for increasing or decreasing the voltage from the D.C. power source (not shown), as is known in the art, to provide an appropriate charging voltage. Charge unit 300 has three clips 304, 306, and 308, for engaging pins 112, 114, and 116, respectively, of portable charge unit 100 or for engaging pins 38, 40, and 42, respectively, of ion inhaler 20. Clip 304 is connected to the negative terminal of the D.C. source 302. Clip 306 is connected to the positive terminal of D.C. source 302. Thus, clips 304 and 306 provide a D.C. charge current to either battery 108 when connected to portable charge unit 100 or to charge storage capacitor 30 when connected to ion inhaler 20. Clip 308 is connected to ground, to ground the charge drain capacitor 32 where connected thereto. Ion inhaler 20 can be connected directly to D.C. charge unit 300 or portable charge unit 100 can be interposed between ion inhaler 20 and D.C. charge unit 300.

OPERATION

The ion inhaler device 20 is prepared for use by charging the charge storage capacitor 30 via the three-pin connector 38. When the charge storage capacitor 30 is sufficiently charged, the personal ion inhaler device 20 is ready for use.

If desired, the mouthpiece 82 is threaded from the tubular section 24 to introduce a substance such as a medicine, scent, or flavoring into chamber 80. Once chamber 80 is filled, mouthpiece 82 is threaded back onto tubular section 24.

The user puts mouthpiece 82 in his or her mouth and draws air through the tubular section 24. This drawing action causes shuttle 66 to move rearwardly against spring 70 allowing coating 78 on shuttle 66 to complete the circuit between contact rings 72 and 74, and complete the circuit between the charge storage capacitor 30 and the ionizer electrode 56.

Thus energized, electrode 56 can ionize the air passing through ionization chamber 50. This air is first filtered by being drawn through filter 46 at the inlet end 44 of tubular section 24. The user is thus provided with a clean, filtered supply of negatively ionized air. This can be for therapeutic purposes or as a substitute for smoking.

There are various changes and modifications which may be made to the invention as would be apparent to those skilled in the art. However, these changes or modifications are included in the teaching of the disclosure, and it is intended that the invention be limited only by the scope of the claims appended hereto.

I claim:

1. A personal ion inhaler comprising:
   a tube with an air passage therethrough having inlet and outlet ends;
   a filter means in the air passage near the inlet end;
   a mouthpiece at the outlet end;
   an ionization chamber in the air passage;
   an electrode in the chamber;
   an electric charge storage device; and, means for automatically connecting said charge storage device to said electrode in response to air flow through the air passage to energize the electrode to ionize the air passing the electrode and disconnecting said charge storage device from said electrode in response to no air flow through the air passage.

2. The personal ion inhaler of claim 1 wherein the charge storage device comprises a capacitor.

3. The personal ion inhaler of claim 2 comprising a conductive lining inside the chamber, a second capacitor, and means for connecting the second capacitor to the conductive lining to reduce static charge accumulated on the conductive lining.

4. The personal ion inhaler of claim 1 further comprising a socket for engaging a recharging device, the socket comprising at least two connectors connected to the charge storage device to conduct a charging D.C. current from the recharging device to the charge storage device.

5. The personal ion inhaler of claim 4 further comprising a portable recharging device, the portable recharging device comprising a charge storage device of greater capacity than the charge storage device of the ion ihaler, and a first set of at least two connectors to engage the connectors in the socket on the ion inhaler to provide a charging D.C. current to the charge storage device of the ion inhaler, the portable recharging device further comprising a second set of at least two connectors for engaging a permanent recharging device, the connectors of the second set connected to the charge storage device of the portable recharging device to conduct a charging D.C. current from the permanent recharging device to the charge storage device in the portable recharging device.

6. The personal ion inhaler of claim 5 further comprising a permanent charging device, the permanent charging device having means for connecting to a source of current, and having a set of at least two connectors to engage the second set of connectors on the portable charging device to supply a charging D.C. current to the charge storage device of the portable charging unit, the set of connectors also being adapted to engage the connnectors on the personal ion inhaler to supply a charging D.C. current to the charge storage device of the personal ion inhaler.

7. The personal ion inhaler of claim 6 wherein the permanent charging device has means for connecting to a source of A.C. current, and wherein the permanent charging device further comprises a voltage transformer and a D.C. voltage rectifier to provide a D.C. charging current.

8. The personal ion inhaler of claim 1 further comprising a generally cylindrical housing for containing the charge storage device, the housing positioned near the inlet end of the tube like the bowl on a pipe.

9. The personal ion inhaler of claim 1 wherein the means for connecting the charge storage device and the electrode comprises:
   a first contact connected to the electrode and a second contact connected to the charge storage device, the first and second contacts being separated in the air passage;
   a shuttle in the air passage, the shuttle slideable between a forward position toward the inlet end and a rearward position toward the outlet end; means for resiliently biasing the shuttle to its forward position, the biasing means allowing the shuttle to be drawn to the rearward position when air is drawn through the passage, the shuttle having an electrically conductive portion that only connects the contacts when the shuttle is in its rearward position.

10. A personal ion inhaler comprising:
    a tube with an air passage therethrough having an inlet and outlet end;
    a filter means in the air passage near the inlet end;
    a mouthpiece at the outlet end;
    an ionization chamber in the air passage;
    an electrode in the chamber;
    an electric charge storage capacitor;
    means for automatically connecting said charge storage device to said electrode in response to air flow through the air passage to energize the electrode to ionize the air passing the electrode and disconnecting said charge storage device from said electrode in response to no air flow through the air passage.

11. The personal ion inhaler of claim 10 further comprising a conductive lining inside the chamber, a charge drain capacitor connected to the conductive lining of the ionization chamber, and wherein the socket comprises a third connector, connected to the charge drain capacitor, to connect the charge drain capacitor to ground during recharging.

12. The personal ion inhaler of claim 10 further comprising a reclosable chamber in the air path in which a substance can be placed to introduce the substance into the air stream drawn through the inhaler.

13. The personal ion inhaler of claim 10 further comprising a generally cylindrical housing for containing the charge storage device, the housing positioned near the inlet end of the tube like the bowl on a pipe.

14. The personal ion inhaler of claim 10 wherein the means for connecting the charge storage device and the electrode comprises:
    a first contact connected to the electrode and a second contact connected to the charge storage device, the first and second contacts being separated in the air passage; and,
    a shuttle in the air passage, the shuttle slideable between a forward position toward the inlet end and a rearward position toward the outlet end; means for resiliently biasing the shuttle to its forward position, the biasing means allowing the shuttle to be drawn to the rearward position when air is drawn through the passage, the shuttle having an electrically conductive portion that only connects the contacts when the shuttle is in its rearward position.

15. A personal ion inhaler comprising:
    a tube with an air passage therethrough having an inlet and outlet end;
    a filter means in the air passage near the inlet end;
    a mouthpiece at the outlet end;
    an ionization chamber in the air passage;
    an electrode in the chamber;
    an electric charge storage capacitor;
    a generally cylindrical housing for containing the charge storage capacitor, the housing position near the inlet end of the tube lime a bowl on a pipe;
    means for automatically connecting said charge storage device to said electrode in response to air flow through the air passage to energize the electrode to ionize the air passing the electrode and disconnecting said charge storage device from said electrode in response to no air flow through the air passage; and,
    a socket for engaging a recharging device, the socket comprising at least two connectors, connected to the opposite leads of the charge storage capacitor to conduct a charging D.C. current from a recharging device to the charge storage capacitor.

16. The personal ion inhaler of claim 15 further comprising a conductive lining in the chamber, a charge drain capacitor connected to the conductive lining of the ionization chamber, and wherein the socket comprises a third connector, connected to the capacitor, to connect the charge drain capacitor to ground during recharging.

17. The personal ion inhaler of claim 16 wherein the means for connecting the charge storage device and the electrode comprises:
- a first contact connected to the electrode and a second contact connected to the charge storage device, the first and second contacts being separated in the air passage; and,
- a shuttle in the air passage, the shuttle sideable between a forward position toward the inlet end and a rearward position toward the outlet end; means for resiliently biasing the shuttle to its forward position, the biasing means allowing the shuttle to be drawn to the rearward position when air is drawn through the passage, the shuttle having an electrically conductive portion that only connects the contacts when the shuttle is in its rearward position.

18. The personal ion inhaler of claim 17 further comprising a portable recharging device, the portable recharging device comprising a charge storage device of greater capacity than the charge storage device of the ion inhaler, and a first set of at least two connectors to engage the connectors in the socket on the ion inhaler to provide a charging D.C. current to the charge storage device of the ion inhaler, the portable recharging device further comprising a second set of at least two connectors for engaging a permanent recharging device, the connectors of the second set connected to the charge storage device of the portable recharging device to conduct a charging D.C. current from the permanent recharging device to the charge storage device in the portable recharging device.

19. The personal ion inhaler of claim 18 further comprising a permanent charging device, the permanent charging device having means for connecting to a source of current, and having a set of at least two connectors to engage the second set of connectors on the portable charging device to supply a charging D.C. current to the charge storage device of the portable charging unit, the set of connectors also being adapted to engage the connnectors on the personal ion inhaler to supply a charging D.C. current to the charge storage device of the personal ion inhaler.

20. The personal ion inhaler of claim 19 wherein the permanent charging device has means for connecting to a source of A.C. current, and wherein the permanent charging device further comprises a voltage transformer and a D.C. voltage rectifier to provide a D.C. charging current.

* * * * *